United States Patent [19]

Sawyer et al.

[11] Patent Number: 5,358,657
[45] Date of Patent: Oct. 25, 1994

[54] REACTIVE COMPOSITIONS CONTAINING SUPEROXIDE ION FOR THE DEGRADATION OF HALOGENATED ORGANIC COMPOUNDS

[75] Inventors: Donald T. Sawyer; Seungwon Jeon; Paul K. S. Tsang, all of College Station, Tex.

[73] Assignee: Texas A&M University System, College Station, Tex.

[21] Appl. No.: 609,630

[22] Filed: Nov. 5, 1990

Related U.S. Application Data

[63] Continuation-in-part of Ser. No. 455,571, Dec. 22, 1989, Pat. No. 5,143,710.

[51] Int. Cl.$^5$ ............................................. C09K 3/00
[52] U.S. Cl. .............................. 252/183.13; 588/206; 588/207; 588/901
[58] Field of Search ............... 423/581; 252/183.13; 588/206, 207, 901

[56] References Cited

U.S. PATENT DOCUMENTS

| | | | |
|---|---|---|---|
| 2,647,934 | 8/1953 | Hillyer et al. | 252/183.13 |
| 3,260,570 | 7/1966 | Russell | 423/581 |
| 4,410,402 | 10/1983 | Sawyer et al. | 588/206 |
| 4,468,297 | 8/1984 | Sawyer et al. | 588/206 |

*Primary Examiner*—Wayne Langel
*Attorney, Agent, or Firm*—Curtis, Morris, Safford

[57] ABSTRACT

Reagent compositions suitable for use in degrading and detoxifying polyhalogenated organic compounds comprising an aprotic solvent having dissolved therein (a) an effective amount of hydrogen donor, (b) an effective amount of a compound which produces hydroxide ion or alkoxide ion, and (c) dioxygen, are shown. These reagent compositions may be used to produce superoxide ion in situ for use in a variety of industrial applications to degrade halogenated hydrocarbons, e.g., PCBs. The generation of superoxide ion may be catalyzed by the presence of anthraquinone and derivatives thereof. Reagent compositions containing (a) an effective amount of hydrogen donor, e.g., hydroxylamine, (b) an effective amount of a compound which produces hydroxide ion or alkoxide ion and (c) dioxygen are also shown. In preferred methods the dioxygen is bubbled through the solutions to continuously form superoxide ion.

3 Claims, 1 Drawing Sheet

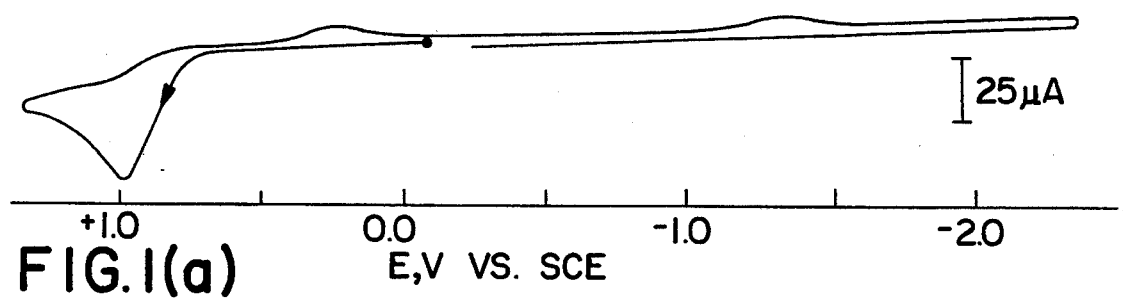
FIG.I(a)  E,V VS. SCE
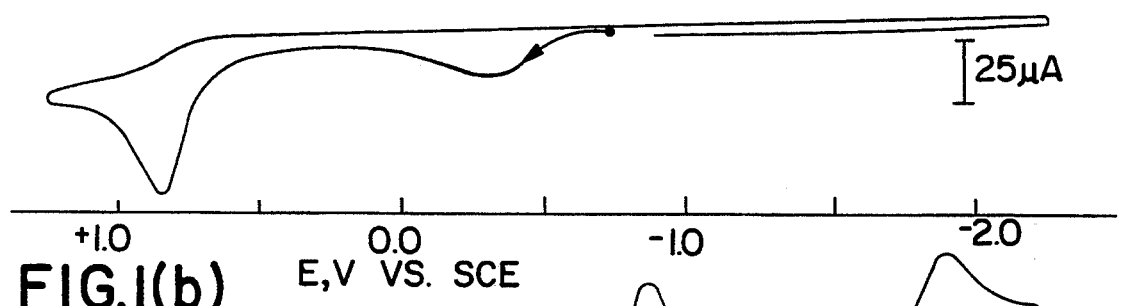
FIG.I(b)  E,V VS. SCE
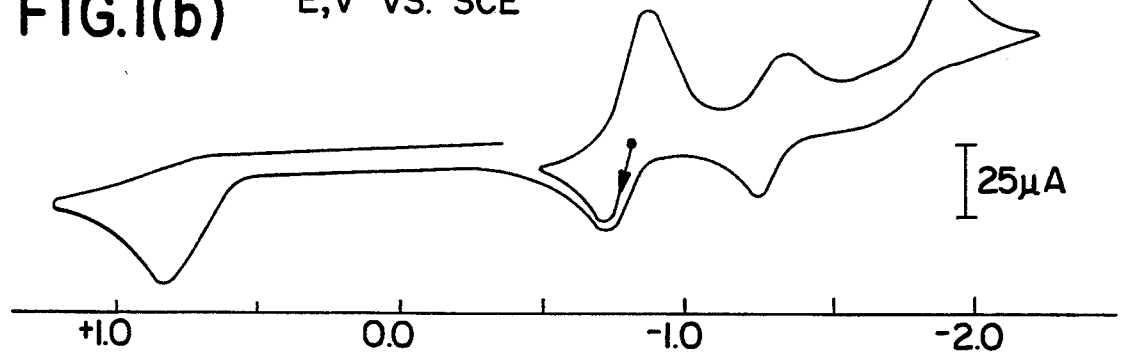
FIG.I(c)  E,V VS. SCE
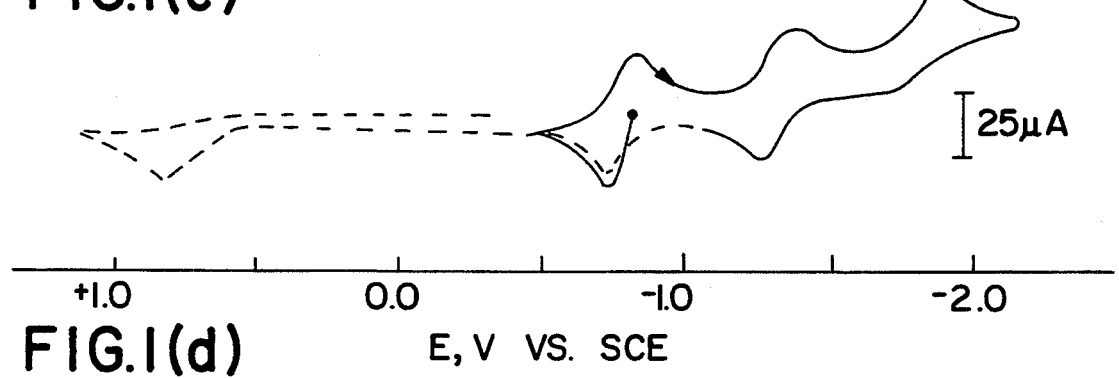
FIG.I(d)  E,V VS. SCE

5,358,657

REACTIVE COMPOSITIONS CONTAINING SUPEROXIDE ION FOR THE DEGRADATION OF HALOGENATED ORGANIC COMPOUNDS

ACKNOWLEDGEMENT

The U.S. Government has rights in this invention pursuant to Grant No. CHE-8516247 awarded by the National Science Foundation.

PRIOR APPLICATIONS

This application is a continuation-in-part of application Ser. No. 07/455,571 filed Dec. 22, 1989, U.S. Pat. No. 5,143,710.

BACKGROUND OF THE INVENTION

The invention broadly relates to reactive compositions containing superoxide ion, to methods for preparing those compositions and to methods for using them in degrading and detoxifying halogenated organic compounds.

The hazard to health and to the environment caused by synthetic halogen-containing organic chemicals is well understood. Compounds such as polychlorinated biphenyls (PCBs), dichlorodiphenyltrichloroethane (DDT), decachlorocatahydro-1,3,4-metheno-2H-cyclobuta [c,d]-pentalen-2-one(Kepone®), and 2,4,5-trichlorophenoxyacetic acid, (2,4,5-T), have been found to be persistent environmental poisons, and, therefore, to require a safe and effective means of disposal.

Halogenated organic compounds are difficult to degrade because of the highly stable nature of the carbon-halogen bonds present in those compounds. These compounds are not only resistant to biodegradation, they cannot be degraded in a practical and effective manner by any of the conventional chemical decomposition methods. In most cases, methods, such as chlorolysis, catalytic dehydrohalogenation, molten salt reactions, ozone reactions, and alkali metal reduction, do not achieve complete dehalogenation. Moreover, these prior art methods typically require expensive reagents, inert atmospheres, extensive temperature control, complex apparatus, and substantial energy consumption.

PCBs present a particularly serious disposal problem. Although PCBs were once widely used because of their excellent insulating properties, as dielectric fluids in electrical equipment such as transformers and capacitors, all such use has been banned by the U.S. Environmental Protection Agency (EPA), because it has been found that they accumulate in human fatty tissue and are extremely toxic. Incineration has been viewed as a practical method for achieving the complete decomposition of PCBs. Incineration of PCB-contaminated materials is wasteful, however, since potentially recyclable materials, such as dielectric and hydraulic fluids, which may contain a relatively small amount of PCBs, are destroyed in the process. To avoid such waste, it has been proposed to treat recyclable materials contaminated by PCBs with an absorbent, e.g., by passing the material through a bed of activated charcoal or a resin to selectively remove the PCBs from said material. The disposal of absorbed PCBs remains a difficult problem.

Significant quantities of waste-containing halogenated organic compounds are presently stored by manufacturers, processors, or consumers. These chemicals must be disposed of in an environmentally acceptable manner. Efforts to develop a safe, practical and effective process for their disposal are continuing. Often such wastes are either incinerated or are stored in dumps for toxic wastes. In the past, negligence in locating such dumps has had catastrophic consequences in exposing large populations to toxic compounds. As a result, massive clean-up efforts are being undertaken to degrade and detoxify these compounds.

Several chemical methods for decomposition of PCBs have been proposed. In one method, high surface sodium, sodium/naphthalene, and sodium naphthalide are employed. These methods are limited, however, because the reagents are difficult to prepare, expensive to ship and unstable in storage. Moreover, the sodium-containing decomposition reagents are sensitive to oxygen and to water and therefore cannot be used reliably. Other methods include those described in U.S. Pat. Nos. 4,400,552, 4,417,977, and 4,602,994, the so-called KPEG or NaPEG processes.

There is thus a clear need for an efficient and safe method to degrade toxic halogenated waste to harmless and environmentally compatible products. However, such a method has been elusive because of certain basic considerations with respect to the nature of toxic halogenated compounds. One aspect of the problem relates to the wide diversity of such compounds. The compounds range from such simple molecules as carbon tetrachloride and chloroform to complex insecticides such as p-p'dichlorodiphenyltrichloroethane (p-p' DDT).

Superoxide ion, which is an effective nucleophile, has proven particularly effective for destroying halogenated organic compounds such as polychlorinated biphenyls (PCBs) and similar toxic materials that create environmental hazards. U.S. Pat. Nos. 4,468,297 and 4,410,402 describe the use of superoxide ion for degrading halogenated organic compounds and halogenated olefinic hydrocarbons.

While halogenated hydrocarbons typically react slowly or incompletely with traditional bases, and this becomes an even more significant problem as the number of halogen atoms in the compound increases, superoxide ion overcomes this difficulty, and reacts rapidly with halogenated hydrocarbons when the reaction is carried out in an aprotic solvent.

Several methods have been developed to generate superoxide ion, including, e.g., pulse radiolysis of dioxygen, Gebicki et al., *J. Am. Chem. Soc.* 1982, 104, 796, photolysis of hydrogen peroxide in aqueous media, McDowell et al., *Inorg. Chem.* 1983, 22, 847 and base-induced decomposition of hydrogen peroxide, Morrison et al., *Inorg. Chem.* 1979, 18, 1971. Solutions of superoxide ion in aprotic solvents have been prepared using electrochemical means. Sawyer et al., *Anal. Chem.* 1982, 54, 1720. The superoxide ion used for degrading halogenated hydrocarbons in U.S. Pat. Nos. 4,468,297 and 4,410,402 is generated in a controlled potential electrolysis cell which uses aprotic solvent for the electrolyte.

The known methods for generating superoxide ion have several disadvantages. Methods for generating superoxide ion based on pulse radiolysis, photolysis, or electrolysis, all require radiation or electrical energy sources. Typically, the energy costs for these methods are prohibitively high, especially for applications such as degrading halogenated hydrocarbons on an industrial scale. Likewise, methods for generating superoxide ion based on decomposing hydrogen peroxide are prohibitively expensive for many applications due to the cost of hydrogen peroxide. Consequently, other methods for generating superoxide ion are desired.

The art has thus not solved the problem of efficient degradation and detoxification of halogenated organic compound wastes. In particular, while methods employing liquid phase reagents containing superoxide ion have shown some promise, methods known to the art are technically difficult, expensive or impractical to use in industrial and soil-remediation projects.

OBJECTS OF THE INVENTION

It is thus a primary object of the invention to provide reagent compositions which are particularly adapted for efficient use in processes for the degradation of halogenated organic compounds.

It is a further and related object of this invention to provide methods for efficiently preparing reactive reagent compositions for use in a variety of industrial and soil-remediation circumstances for the efficient, cost effective destruction of halogenated organic compounds, including PCBs.

It is still a further object of this invention to provide liquid phase reagent compositions which develop large concentrations of superoxide ion capable of attacking halogenated, and particularly chlorinated hydrocarbon compounds which are conventionally believed to be relatively unreactive.

It is still a further object of this invention to provide methods for conducting industrial processes for the destruction of compounds containing toxic wastes comprising PCBs and other chlorinated compounds.

SUMMARY OF THE INVENTION

These and other objects of the invention are obtained by employing liquid phase reagent compositions comprising solutions, in an aprotic solvent, of a hydrogen donor, e.g., a primary or secondary aromatic amine, or phenylhydrazine or substituted phenylhydrazine, a compound which produces hydroxide or alkoxide ion and dioxygen. The reagent composition forms superoxide which is then available for the intended purposes of degrading a halogenated organic compound. In a preferred embodiment, an anthraquinone or substituted anthraquinone compound is used together with certain hydrogen donors to generate superoxide.

In another embodiment of the invention, the hydrogen donor is replaced with a proton donor, e.g., hydroxylamine.

The reactive compositions of the invention are prepared by forming a solution of the three components or by forming a solution of the hydrogen donor and source of hydroxide or alkoxide ion, and thereafter introducing dioxygen.

The nature of the compositions and the ease of generating the superoxide ion in situ, make the compositions and methods particularly adapted for effective use in processes for the destruction of halogenated hydrocarbons, e.g., in the treatment of liquid phase waste products, the remediation of soils, and in many other uses as well.

BRIEF DESCRIPTION OF THE DRAWINGS

FIG. 1 depicts cyclic voltammograms for (a) aniline (PhNH$_2$); (b) aniline (PhNH$_2$) in the presence of hydroxide ion (OH$^-$); (c) aniline (PhNH$_2$) in the presence of hydroxide ion (OH$^-$) and dioxygen (O$_2$); and (d) the product solution of (c) after deaeration with argon (Ar).

DETAILED DESCRIPTION OF THE INVENTION

The invention is broadly in reagent compositions which contain superoxide ion and have utility in the degradation of polyhalogenated organic compounds. The compositions of the invention are believed to contain superoxide ion although the invention is not limited to the presence of superoxide ion in those compositions. The invention is also in methods for preparing the reagent compositions and in methods for using those reagent compositions to degrade polyhalogenated organic compounds.

In a first embodiment of the invention, the reagent composition comprises an aprotic solvent having dissolved therein (a) an effective amount of a hydrogen donor, (b) an effective amount of a compound which produces hydroxide ion (OH$^-$) or alkoxide ion (OR$^-$), and (c) dioxygen (O$_2$). The composition contains superoxide ion (O$_2^{-\cdot}$). A major advantage of the compositions is that they can be used in a wide variety of circumstances wherein it is advantageous to generate superoxide ion in situ. These ions are generated in solutions of aprotic solvents that contain hydroxide ions (OH$^-$) or alkoxide ions (RO$^-$) and are or become saturated with dissolved dioxygen (O$_2$).

The first embodiment proceeds via a hydrogen transfer mechanism. The preferred hydrogen donors are compounds of the formulae

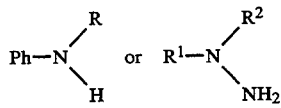

where R is H, lower alkyl containing 1–4 carbon atoms or phenyl, and R$^1$ and R$^2$ may be the same or different and each is H, alkyl of 1–4 carbon atoms or phenyl. They include primary aromatic amines, secondary aromatic amines, and N-substituted hydrazines. The preferred hydrogen donors are aniline, N-methylaniline, N-phenylaniline, phenylhydrazine, 1,1-diphenylhydrazine, and 1-methyl-1-phenylhydrazine.

While not bound by any theory, it appears that the reaction mechanism for the hydrogen transfer method, where aniline (PhNH$_2$) is the hydrogen donor, is as follows:

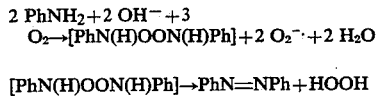

The overall reaction is thus as follows:

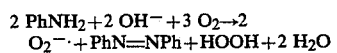

The hydroxide ion (OH$^-$) acts as a one-electron reducing agent towards the dioxygen (O$_2$), and is facilitated by the available hydrogens of the aniline (PhNH$_2$). The aniline (PhNH$_2$) appears to form radicals which are stabilized by radical coupling to dioxygen (O$_2$) to form the intermediate [PhN(H)OON(H)Ph] which in turn decomposes into azobenzene (PhN=NPh) and hydrogen peroxide (HOOH).

N-substituted anilines such as N-methylaniline (PhNHMe) and N-phenylaniline (PhNHPh) also act as hydrogen donors, to give similar yields of superoxide ion when reacted with hydroxide ion and dioxygen in an aprotic solvent. Phenylhydrazine ($PhNHNH_2$), 1,1-diphenylhydrazine ($Ph_2NNH_2$), and 1-methyl-1-phenylhydrazine [$Ph(Me)NNH_2$] also act as hydrogen donors, like aniline, to give similar yields of superoxide ion when reacted with hydroxide ion and dioxygen in an aprotic solvent. The reaction when phenylhydrazine ($PhNHNH_2$) is the hydrogen donor is as follows:

$$2\ PhNHNH_2 + 2\ OH^- + 3\ O_2 \rightarrow 2\ O_2^{-\cdot} + 2\ PhH + 2\ N_2 + HOOH + 2\ H_2O$$

Aprotic solvents are used as the solvents in the compositions of the invention because they are conducive to the reactions necessary to generate the superoxide ion. Such solvents are well known, See Sawyer et al., *Experimental Electrochemistry for Chemists*, John Wiley & Sons, New York, 1974, pp. 167-215. Aprotic solvents generally have hydrogen bound only to carbon and are at best poor hydrogen-bond donors. They are weakly acidic and proton exchange occurs slowly. The presence of acidic hydrogen in the solution interferes with the generation of superoxide ion. Common aprotic solvents include various amides, nitriles, chlorinated hydrocarbons, ethers and other materials. Specific examples include acetone, pyridine, acetonitrile, benzonitrile, adiponitrile, dimethylformamide, N-methyl-2-pyrrolidone, tetrahydrofuran, dioxane, dimethyl sulfoxide, sulfolane, and hexamethylphosphoramide. Preferably, aprotic solvents such as dimethylsulfoxide, dimethylformamide and tetramethylenesulfone are used in the compositions of the invention. Dimethylsulfoxide is preferred over other aprotic solvents, however, because it deactivates water which reacts with superoxide ion.

Still another class of aprotic solvents which can be used to advantage include the monoalkyl and dialkyl ethers (wherein the alkyl group is a lower alkyl containing from 1-4 carbon atoms) of alkylene, dialkylene or polyalkylene glycol having from 2-4 carbon atoms in the alkylene group. Such compounds may include mixtures of alkyl and or alkylene groups having 1-4 or 2-4 carbon atoms in the ether and/or chain moieties, respectively. Preferred compounds in such class include polyethylene glycol and its monomethyl and dimethyl ether derivatives, glyme, diglyme, triglyme and tetraglyme.

Many compounds may be used as the source of hydroxide ion or alkoxide ion in the aprotic solvent. Among them are alkali or alkaline earth metal oxides, bimetallic oxides, hydroxides, carbonates, bicarbonates, phosphates, and alkoxides with 1-4 carbon atoms. Also useful are compounds of the formula $(R^3)_4$—N—$OR^4$ where $R^3$ is lower alkyl of 1-4 carbon atoms and $R^4$ is hydrogen, and complexes comprising the reaction products of an alkali metal or alkali metal hydroxide, a liquid polyglycol or polyglycol monoalkyl ether and oxygen. The latter complexes are described in, e.g., U.S. Pat. Nos. 4,417,977 and 4,471,143 to Pytlewski et al., and are often referred to as NaPEG, KPEG, etc. These complexes may be added to the aprotic solvent or may be formed in situ by the reaction in the aprotic solvent of an alkali metal hydroxide, the liquid polyglycol (which may itself comprise the aprotic solvent), and dioxygen. Representative sources of hydroxide or alkoxide include ($Bu_4N$) OH, ($Me_4N$) OH.$5H_2O$, KOH, NaOH, Na(PEG), K(PEG), K(MePEG), Na(MePEG), ($Bu_4N$)PEG, ($Me_4N$)PEG, KOMe, NaOMe, ($Me_4N$)OMe, $K_2CO_3$, $Na_2CO_3$, $CaCO_3$, $KHCO_3$, $NaHCO_3$, $K_3PO_4$, $Na_3PO_4$, CaO, $NaAlO_2$, and $Na_2ZnO_2$. The common alkali metal hydroxides are most economical and therefore preferred.

It has been found that certain catalysts can effectively catalyze the hydrogen transfer method. The catalysts are selected from the group consisting of quinones, phenazines and flavins.

Preferred among the catalysts are anthraquinone and its derivatives. While not being bound by any theory, it appears that anthraquinone catalyzes the reaction of hydrazine with hydroxide ion and dioxygen. The reaction mechanism appears to be:

$$AQ + OH^- \rightleftharpoons [AQ(OH)^-]$$

$$[AQ(OH)^-] + \tfrac{1}{2} H_2NNH_2 \rightarrow AQ^{-\cdot} + H_2O + \tfrac{1}{2} N_2$$

$$AQ^{-\cdot} + O_2 \rightleftharpoons AQ + O_2^{-\cdot}$$

No anthraquinone (AQ) is consumed in the reaction and thus the overall reaction is:

$$H_2NNH_2 + 4\ O_2 + 4\ OH^- \rightarrow 4\ O_2^{-\cdot} + N_2 + 4\ H_2O$$

Dioxygen is preferably not added to the solution until the first step of the reaction has reached equilibrium.

Other quinones effective for catalyzing the reaction between hydrazine, hydroxide ions, and dioxygen are 2-ethylanthraquinone (2-EtAQ), 2-methylanthraquinone (2MeAQ), 1,4-naphthaquinone (NQ), and 1,4-benzoquinone (Q). The relative reaction rates for the quinones are in the order 2-EtAQ ~ 2-MeAQ > AQ > NQ > Q. Similar catalytic effects are also obtained for hydrated quinones.

Anthraquinone has also been used to catalyze a reaction between 1,4-cyclohexadiene (1,4-CHD), as a hydrogen donor instead of hydrazine, with hydroxide ion and dioxygen to produce superoxide ion. The overall reaction appears to be:

$$2O_2 + 2\ OH^- + 1,4\text{-CHD} \rightarrow 2\ O_2^{-\cdot} + 2\ H_2O + PhH$$

Dimethyl sulfoxide is preferred over dimethylformamide and acetonitrile as the aprotic solvent in this reaction because only low concentrations of superoxide ion are present in these solvents when the reaction is carried out. It appears that the water produced by the reaction disproportionates the superoxide ion and reduces the yield of superoxide ion when dimethylformamide and acetonitrile are the aprotic solvent. Dimethyl sulfoxide, on the other hand, deactivates water and tends to avoid this effect.

In another embodiment of the invention, the compositions include a proton donor instead of a hydrogen donor in order to create, by a proton transfer mechanism, the desired superoxide ion. In the proton transfer method, the desired compounds to effect proton transfer include those having the formula:

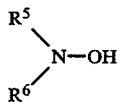

where $R^5$ and $R^6$ may be the same or different and each is H or lower alkyl of 1-4 carbon atoms.

These compounds together with the compounds which provide hydroxide or alkoxide ions and dioxygen generate superoxide ion. The preferred proton donors are hydroxylamine, N-methylhydroxylamine and N,N'- dimethylhydroxylamine. The aprotic solvents are those used in the hydrogen transfer method.

While not being bound by theory, the reaction mechanism where hydroxylamine is the proton donor appears to be as follows:

$$H_2NOH + OH^- \rightarrow H_2NO^- + H_2O$$

$$2\ H_2NO^- + 2\ O_2 \rightarrow 2\ H_2NO\cdot + 2\ O_2^{-\cdot}$$

$$2\ H_2NO\cdot \rightarrow [H_2NOONH_2]$$

$$[H_2NOONH_2] + 2\ OH^- + 2\ O_2 \rightarrow 2\ NO_2^- + HOOH + 2\ H_2O$$

The overall reaction is:

$$2H_2NOH + 4\ OH^- + 4\ O_2 \rightarrow 2\ O_2^{-\cdot} + 2\ NO_2^- + HOOH + 4\ H_2O$$

In the first step of the reaction, the hydroxylamine ($H_2NOH$) is deprotonated by hydroxide ion ($OH^-$) to form the anion ($H_2NO^-$) and water ($H_2O$). In the second step the anion ($H_2NO^-$) gives up an electron to dioxygen ($O_2$) to form the radical ($H_2NO\cdot$) and superoxide ion ($O_2^{-\cdot}$). Two of the radicals ($H_2NO\cdot$) are stabilized by coupling to give an intermediate [$H_2NOONH_2$], which in turn reacts with hydroxide ion ($OH^-$) and dioxygen ($O_2$) to give nitrite ion ($NO_2^-$), hydrogen peroxide (HOOH), and water ($H_2O$).

It appears that the oxygen atom of the hydroxylamine is involved in attack on the dioxygen because O-methylhydroxylamine and O-benzylhydroxylamine have proven unreactive in this context. In contrast, N-methylhydroxylamine and N,N'-dimethylhydroxylamine are rapidly oxidized in alkaline aprotic solutions.

The compositions of the invention can be prepared by several different methods. In its broadest embodiment, the composition can be prepared by forming a solution, in an aprotic solvent, of the hydrogen donor, the compound which produces hydroxide ion or alkoxide ion and dioxygen. If it is desired to catalyze the system, then the catalyst can be added to the solution as well. Where proton transfer mechanisms are involved, likewise, in its broadest embodiment, the reagent composition can be prepared by mixing, in any order, the proton donor, the compound which produces hydroxide ion or alkoxide ion and dioxygen.

In a preferred method, a solution of the hydrogen donor or proton donor and the source of hydroxide or alkoxide ion is formed in the desired aprotic solvent and thereafter dioxygen is dissolved in that solution by bubbling dioxygen gas through it.

In still a further preferred embodiment the compound that provides the source of hydroxide or alkoxide ion is first added to the aprotic solvent, then the hydrogen donor or proton donor is added and thereafter dioxygen gas is bubbled through the solution. In catalyzed hydrogen transfer systems, the anthraquinone or other catalyst is added after the other compounds are dissolved in the aprotic solvent, and, after the system has reached equilibrium, dioxygen is added to the solution. In all cases the formation of superoxide ion proceeds as the dioxygen is bubbled through the solution. It will be apparent to those skilled in the art that different procedures may be adopted for the preparation of superoxide depending upon the circumstances of use.

It is a major advantage of the invention that reagent compositions containing superoxide can be used to degrade and detoxify polyhalogenated organic compounds. Representative polyhalogenated organic compounds which may be degraded by contact with the compositions of the invention include hexachlorocyclohexane, hexachlorobenzene, trichlorobenzene, tetrachlorobenzene, dichlorodiphenyltrichloroethane, decadichlorooctahydro -1,3,4-metheno-2H-cyclobuta-[c,d]-pentalen-2-one, tetrachlorodibenzo-p-dioxin (TCDD), and polychlorinated biphenyls. The invention is particularly useful for the decomposition of PCBs. Brominated or fluorinated analogues of any of the aforementioned compounds may also be degraded using the processes of the invention.

The degradation reactions may be carried out by contacting a substance, e.g., soil, containing a halogenated organic compound, e.g., PCBs, with the composition of the invention, or, the contaminated substances may be contacted with aprotic solvent containing hydrogen donor or proton donor and a source of hydroxide or alkoxide ion, and thereafter dioxygen may be introduced into that solution in contact with the substance in order to generate superoxide ion in situ.

The compositions of the invention may be reacted with a variety of materials, including transformer oils, wastes from chemical process plants, soils, and other materials. It is well within the scope of the art to adapt the compositions and methods of the invention to effectively treat a variety of materials.

Compositions of the invention provide an economical way of decomposing halogenated organic compounds. They may be made from relatively inexpensive starting materials and no specialized equipment is required in connection with their preparation or use. The compositions may be used effectively to produce superoxide in situ for use in a multitude of applications using air as the source of dioxygen. The compositions are extremely effective because they react with a broad spectrum of polyhalogenated organic compounds and substantially completely dehalogenate the carbon-halogen bonds under moderate reaction conditions.

The invention is further illustrated by the following examples:

EXAMPLE 1

Experiments were conducted to determine the ability of aniline, N-substituted aniline and phenylhydrazine, to generate superoxide ion when reacted with hydroxide ion and dioxygen in an aprotic solvent.

A solution of aniline ($PhNH_2$) in dimethyl sulfoxide which was saturated with dioxygen ($O_2$) was prepared. The solution included concentrations of 5.5 mM (millimolar) of aniline and 2.1 mM of dioxygen (at 1 atmosphere). The dimethyl sulfoxide used was "distilled in glass" grade without further purification. The aniline used was "99.5+ percent pure" and was used without further purification.

Excess hydroxide ion ($OH^-$) in the form of tetrabutylammonium hydroxide [($Bu_4N$)OH] was added to the solution to achieve a concentration of 22 mM of $OH^-$ ion. The tetrabutylammonium hydroxide and other reagents used were analytical grade or the highest available grade and were used without further purification.

The excess hydroxide ion ($OH^-$), dissolved dioxygen ($O_2$), and aniline ($PhNH_2$) reacted in the dimethyl sulfoxide solution to form superoxide ion ($O_2^{-\cdot}$), azobenzene (PhN=NPh), hydrogen peroxide (HOOH), and water ($H_2O$). The dioxygen was introduced by bubbling gaseous dioxygen through the solution of other reactants for 20 minutes, and then purging with argon. The reaction yielded concentrations of 1.4 mM of superoxide ion and 2.5 mM of azobenzene.

Table 1 indicates the yields of superoxide ion ($O_2^{-\cdot}$) and azobenzene (PhN=NPh) in both mM concentration and % yield of the stoichiometrically expected amount according to the reaction for the hydrogen transfer method when aniline is the hydrogen donor for various starting concentrations of aniline ($PhNH_2$) and various amounts of excess hydroxide ion ($OH^-$).

TABLE 1

| Yields of $O_2^{-\cdot}$ and PhN=NPh, mM (%) | | |
|---|---|---|
| $PhNH_2$ mM | $O_2^{-\cdot}$ mM (%) | PhN=NPh mM (%) |
| 1:1 $OH^-$:$PhNH_2$ mol-ratio (unreacted $PhNH_2$ present): | | |
| 1.1 | 0.3(30) | 0.2(33) |
| 2.2 | 0.4(19) | 0.4(35) |
| 5.5 | 0.7(13) | 0.9(34) |
| 11.0 | 1.3(12) | 2.4(43) |
| 2:1 $OH^-$:$PhNH_2$ mol-ratio (unreacted $PhNH_2$ present): | | |
| 1.1 | 0.4(40) | 0.3(56) |
| 2.2 | 0.6(26) | 0.7(63) |
| 5.5 | 1.1(20) | 1.6(59) |
| 11.0 | 1.5(14) | 3.3(60) |
| 4:1 $OH^-$:$PhNH_2$ mol-ratio: | | |
| 1.1 | 0.6(51) | 0.5(87) |
| 2.2 | 1.0(47) | 0.9(84) |
| 5.5 | 1.4(26) | 2.5(89) |
| 11.0 | 2.4(22) | 4.9(89) |
| 10:1 $OH^-$:$PhNH_2$ mol-ratio: | | |
| 1.1 | 1.1(97) | 0.5(93) |
| 2.2 | 1.9(84) | 1.0(91) |
| 5.5 | 2.0(36) | 2.6(93) |
| 11.0 | 1.6(15) | 5.0(91) |

The yields of superoxide ion and azobenzene were determined by linear sweep voltammetry. The azobenzene concentration was also determined by UV absorption spectroscopy.

FIG. 1 depicts cyclic voltammograms for: (a) aniline dissolved in dimethyl sulfoxide at a concentration of 2 mM; (b) the solution of (a) to which hydroxide ion has been added to achieve a hydroxide ion to aniline mol-ratio of 2:1; (c) the solution of (b) with dioxygen dissolved in the solution at one atmosphere; and (d) the product solution of (c) after purging the solution with argon. The depth of the minimum for the curve at −0.7 V in voltammograms (c) and (d) indicates the concentration of superoxide ion that has been generated in situ.

Ideally, according to the stoichiometry of the overall equation for the reaction of aniline with hydroxide ion and dioxygen, the moles of superoxide ion generated should be equal to the moles of aniline consumed. The percent yields of superoxide ion ($O_2^{-\cdot}$) in Table 1 indicate that this is not the case. It is believed that residual water causes the superoxide ion to disproportionate according to the following reaction:

$$2\ O_2^{-\cdot} + H_2O \rightarrow O_2 + HOO^- + OH^-$$

Nevertheless, Table 1 indicates that if a large excess of $OH^-$ is used the amount of superoxide ion produced is very near the stoichiometric amount.

Table 2 indicates the yields of superoxide ion for N-substituted anilines, i.e, N-methylaniline (PhNHMe) and N-phenylaniline (PhHNPh), and for three phenylhydrazines, i.e., phenylhydrazine ($PHNHNH_2$), 1,1-diphenylhydrazine ($Ph_2NNH_2$), and 1-methyl-1-phenylhydrazine [Ph(Me)$NNH_2$].

TABLE 2

| | Yields of $O_2^{-\cdot}$, mM (%) | | |
|---|---|---|---|
| | 2:1 | 4:1 | 10:1 |
| $OH^-$:PhNHMe mol-ratio | | | |
| PhNHMe (mM) | | | |
| 1.8 | 0.6(30) | 0.8(45) | 1.4(77) |
| 4.6 | 1.2(26) | 2.2(48) | 3.4(73) |
| 9.2 | 2.6(28) | 4.8(52) | 4.5(49) |
| $OH^-$:PhNHPh mol-ratio | | | |
| PhNHPh (mM) | | | |
| 2.0 | — | 1.2(60) | 1.8(90) |
| 3.6 | 1.0(26) | — | — |
| 4.6 | — | 2.7(58) | 4.0(88) |
| 10.0 | 1.6(16) | 5.6(56) | 6.9(69) |
| 12.4 | — | 5.9(48) | — |
| $OH^-$:$PhNHNH_2$ mol-ratio | | | |
| $PhNHNH_2$ (mM) | | | |
| 3.5 | — | 0.9(45) | 1.0(50) |
| 5.5 | — | 1.4(28) | 1.8(36) |
| 10.0 | — | 1.8(18) | 2.6(26) |
| $OH^-$:$Ph_2NNH_2$ mol-ratio | | | |
| $Ph_2NNH_2$ (mM) | | | |
| 3.5 | — | 0.6(17) | 1.4(40) |
| 5.1 | — | 1.0(20) | 1.5(29) |
| $OH^-$:Ph(Me)$NNH_2$ mol-ratio | | | |
| Ph(Me)$NNH_2$ (mM) | | | |
| 4.2 | — | 1.0(24) | 1.3(31) |

EXAMPLE II

Experiments were conducted to determine the ability of hydrazine to generate superoxide ion when reacted with dioxygen and hydroxide ion in an aprotic solvent in the presence of anthraquinone or its derivatives. Table 3 indicates the yields of superoxide ion ($O_2^{-\cdot}$) for the reaction between hydrazine ($H_2NNH_2$), hydroxide ion ($OH^-$), and dioxygen ($O_2$) in the presence of anthraquinone (AQ), 2-ethylanthraquinone (2-EtAQ), 2-methylanthraquinone (2-MeAQ), 1,4-naphthaquinone (NQ), and 1,4-benzoquinone (Q).

TABLE 3

| Yields of $O_2^{-\cdot}$, mM (%) | | |
|---|---|---|
| $H_2NNH_2$ mM | $OH^-$ mM | $O_2^{-\cdot}$ mM (%) |
| AQ mM | | |
| 0.5 | 3.0 | 12.0 — 3.8(32) |
| 0.5 | 6.0 | 24.0 — 6.4(27) |
| 0.5 | 9.0 | 36.0 — 8.2(23) |
| 1.0 | 3.0 | 12.0 — 3.5(29) |
| 1.0 | 6.0 | 24.0 — 6.2(26) |
| 1.0 | 9.0 | 36.0 — 7.6(21) |
| 2.0 | 3.0 | 12.0 — 3.1(26) |
| 2.0 | 9.0 | 36.0 — 6.8(19) |
| 2-EtAQ mM | | |
| 1.0 | 3.0 | 12.0 — 3.6(30) |
| 1.0 | 6.0 | 24.0 — 6.3(26) |
| 1.0 | 9.0 | 36.0 — 8.5(24) |
| 2.0 | 3.0 | 12.0 — 3.4(28) |
| 2.0 | 6.0 | 24.0 — 6.1(25) |
| 2.0 | 9.0 | 36.0 — 8.2(23) |
| 2-MeAQ mM | | |
| 1.0 | 3.0 | 12.0 — 3.4(28) |
| 1.0 | 6.0 | 24.0 — 6.2(26) |
| 1.0 | 9.0 | 36.0 — 8.2(23) |
| NQ mM | | |
| 1.0 | 3.0 | 12.0 — 3.3(28) |
| 1.0 | 6.0 | 24.0 — 4.9(20) |
| Q mM | | |
| 1.0 | 3.0 | 12.0 — 3.3(28) |
| 1.0 | 6.0 | 24.0 — 3.6(15) |

EXAMPLE III

Experiments were conducted to determine the ability of hydroxylamine and its derivatives to generate superoxide ion when reacted with dioxygen and hydroxide ion in an aprotic solvent. Table 4 indicates the yields of superoxide ion ($O_2^-\cdot$) for various concentrations of hydroxylamine and its derivatives.

TABLE 4

| | Yield $O_2^-\cdot$ mM (%) | |
| --- | --- | --- |
| | 4:1 | 10:1 |
| In dimethyl sulfoxide solvent: | | |
| $OH^-$:$H_2NOH$ | | |
| $H_2NOH$ mM | | |
| 1.4 | 0.7(50) | 0.9(64) |
| 4.3 | 1.7(37) | 2.0(46) |
| 5.4 | 1.6(30) | 2.0(37) |
| $OH^-$:MeNHOH | | |
| MeNHOH mM | | |
| 4.3 | 1.3(30) | 1.5(35) |
| $OH^-$:Me$_2$NOH | | |
| Me$_2$NOH mM | | |
| 1.8 | 1.0(55) | 1.4(77) |
| 3.8 | 1.3(34) | 1.4(37) |
| 6.5 | 1.5(23) | 1.7(26) |
| In dimethylformamide solvent: | | |
| $OH^-$:$H_2NOH$ | | |
| $H_2NOH$ mM | | |
| 4.6 | 2.4(52) | 3.1(67) |
| 12.4 | 2.4(52) | 4.3(35) |

The apparent yield of superoxide ion was low when hydroxylamine ($H_2NOH$) was used as proton donor because the superoxide ion ($O_2^-\cdot$) reacts with hydroxylamine ($H_2NOH$) to produce nitrous oxide (NO) according to the following reaction:

$$H_2NOH + 3\ O_2^-\cdot \rightarrow NO + 3\ HOO^-$$

The examples and embodiments described above are illustrative of the invention. Changes and modifications can be made without departing from the scope of the invention. It is intended that such changes and modifications fall within the scope of the invention as defined by the claims.

What is claimed is:

1. A reagent composition comprising an aprotic solvent having dissolved therein (a) an effective amount of a hydrogen donor; (b) an effective amount of a compound which produces hydroxide ion or alkoxide ion; (c) a catalyst selected from the group consisting of quinones, phenazines and flavins; and (d) dioxygen.

2. A composition as recited in claim 1 wherein said catalyst is selected from the group consisting of anthraquinone, 2-ethylanthraquinone, 2-methyl-anthraquinone, 1,4-naphthaquinone and 1,4-benzoquinone.

3. A composition as recited in claim 2 wherein said hydrogen donor is hydrazine or 1,4-cyclohexadiene.

* * * * *